(12) United States Patent
Blankfield

(10) Patent No.: US 8,915,860 B2
(45) Date of Patent: Dec. 23, 2014

(54) SYSTEM AND METHOD TO EVALUATE CARDIOVASCULAR HEALTH

(76) Inventor: Robert P. Blankfield, Brecksville, OH (US)

( * ) Notice: Subject to any disclaimer, the term of this patent is extended or adjusted under 35 U.S.C. 154(b) by 0 days.

(21) Appl. No.: 13/642,921

(22) PCT Filed: Nov. 4, 2010

(86) PCT No.: PCT/US2010/055440
§ 371 (c)(1),
(2), (4) Date: Dec. 6, 2012

(87) PCT Pub. No.: WO2011/139297
PCT Pub. Date: Nov. 10, 2011

(65) Prior Publication Data
US 2013/0237875 A1    Sep. 12, 2013

Related U.S. Application Data

(63) Continuation-in-part of application No. PCT/US2010/033493, filed on May 4, 2010.

(60) Provisional application No. 61/175,500, filed on May 5, 2009.

(51) Int. Cl.
| | |
|---|---|
| A61B 5/02 | (2006.01) |
| A61B 5/00 | (2006.01) |
| A61B 5/029 | (2006.01) |
| A61B 5/0205 | (2006.01) |
| A61B 5/0295 | (2006.01) |
| A61B 5/03 | (2006.01) |
| A61B 5/107 | (2006.01) |
| A61B 5/024 | (2006.01) |

(52) U.S. Cl.
CPC ............... *A61B 5/4848* (2013.01); *A61B 5/029* (2013.01); *A61B 5/02035* (2013.01); *A61B 5/0205* (2013.01); *A61B 5/0295* (2013.01); *A61B 5/03* (2013.01); *A61B 5/107* (2013.01); *A61N 5/14546* (2013.01); *A61B 5/4839* (2013.01); *A61B 5/7225* (2013.01); *A61B 5/7275* (2013.01); *A61B 5/7278* (2013.01); *A61B 5/02* (2013.01); *A61B 5/024* (2013.01)
USPC ........................................................ 600/526

(58) Field of Classification Search
None
See application file for complete search history.

(56) References Cited

U.S. PATENT DOCUMENTS

2002/0164598 A1    11/2002 Muhlestein et al.
2002/0193689 A1*   12/2002 Bernstein et al. ............. 600/454
(Continued)

OTHER PUBLICATIONS

Vonk-Noordegraaf, et.al., Physiol. Meas. May 2000;21(2):285-93.*
(Continued)

*Primary Examiner* — Brian T Gedeon
*Assistant Examiner* — Ankit Tejani
(74) *Attorney, Agent, or Firm* — Hahn Loeser & Parks LLP

(57) ABSTRACT

Systems and methods are described herein to evaluate a candidate medication as it relates to a subject's cardiovascular health. A processing component is employed to measure a first value of one or more cardiovascular markers, via a computer, which are associated with a circulatory system of each subject that is to receive the candidate medication. The candidate medication is administered to each subject and a second value of one or more cardiovascular markers are measured subsequent to the administration as of the candidate medication. Continued testing of the candidate medication can be continued dependent upon the change in the one or more cardiovascular markers.

3 Claims, 9 Drawing Sheets

(56) References Cited

U.S. PATENT DOCUMENTS

| | | |
|---|---|---|
| 2004/0267142 A1* | 12/2004 | Paul .............................. 600/509 |
| 2005/0159783 A1* | 7/2005 | Hettrick et al. ................... 607/5 |
| 2006/0106322 A1* | 5/2006 | Arand et al. .................. 600/514 |
| 2007/0214007 A1 | 9/2007 | Hackner |
| 2008/0000801 A1 | 1/2008 | Mackie, Jr. |
| 2008/0275349 A1* | 11/2008 | Halperin et al. .............. 600/484 |
| 2009/0326510 A1 | 12/2009 | Haefner et al. |

OTHER PUBLICATIONS

Biopac Systems, Inc. Application Note 215: Cardiac Output Measurement—Using NICO100C and LEAD130. Updated Sep. 12, 2007.*

\* cited by examiner

US 8,915,860 B2

SYSTEM AND METHOD TO EVALUATE CARDIOVASCULAR HEALTH

CROSS-REFERENCED TO RELATED APPLICATION

This application is a National Stage Entry of International Application No. PCT/US10/55440, filed Nov. 4, 2010, which is a continuation-in-part of co-pending International Application No. PCT/US10/33493, filed May 4, 2010, which claims priority to U.S. Provisional Patent Application Ser. No. 61/175,500, filed May 5, 2009, which are incorporated herewith.

BACKGROUND OF THE INVENTION

The present exemplary embodiments relate generally to cardiovascular function. They find particular application in the quantification and effect of stroke volume and other cardiovascular variation as they relate to the health of the cardiovascular system. It is to be appreciated, however, that the present exemplary embodiments are also amenable to other like applications.

Conventionally, thiazide diuretics and angiotensin converting enzyme inhibitors (ACEIs) are preferred medications for monotherapy of uncomplicated hypertension. Recent evidence suggests that calcium channel blockers (CCBs) should be considered comparable to thiazide diuretics and ACEIs. β-adrenergic receptor blockers (β-blockers) and α-receptor blockers (α-blockers) are typically less preferred as initial pharmacological therapy for uncomplicated hypertension. These different classes of antihypertensive medications differ in their hemodynamic effects and have varying degrees of success in the remedy of cardiovascular conditions. In general, thiazide diuretics are more effective than ACEIs, β-blockers, α-blockers and CCBs at preventing cardiovascular morbidity and mortality.

Formulation-to-market development of a medication is a costly endeavor, generally requiring a significant expenditure of time, capital and resources. Accordingly, early identification of promising formulations is essential. Due to complexities of cardiovascular function, however, it is often difficult to identify specific markers that are associated with desired pharmaceutical results.

BRIEF DESCRIPTION OF THE INVENTION

In one aspect, systems and methods are employed to evaluate a candidate medication as it relates to a subject's cardiovascular health. A processing component is employed to measure a first value of one or more cardiovascular markers, via a computer, which are associated with a circulatory system of each subject that is to receive the candidate medication. The candidate medication is administered to each subject and a second value of the one or more cardiovascular markers are measured subsequent to the administration of the candidate medication. Continued testing of the candidate medication can be continued dependent upon the change in the one or more cardiovascular markers.

DETAILED DESCRIPTION OF THE INVENTION

Figure 1:
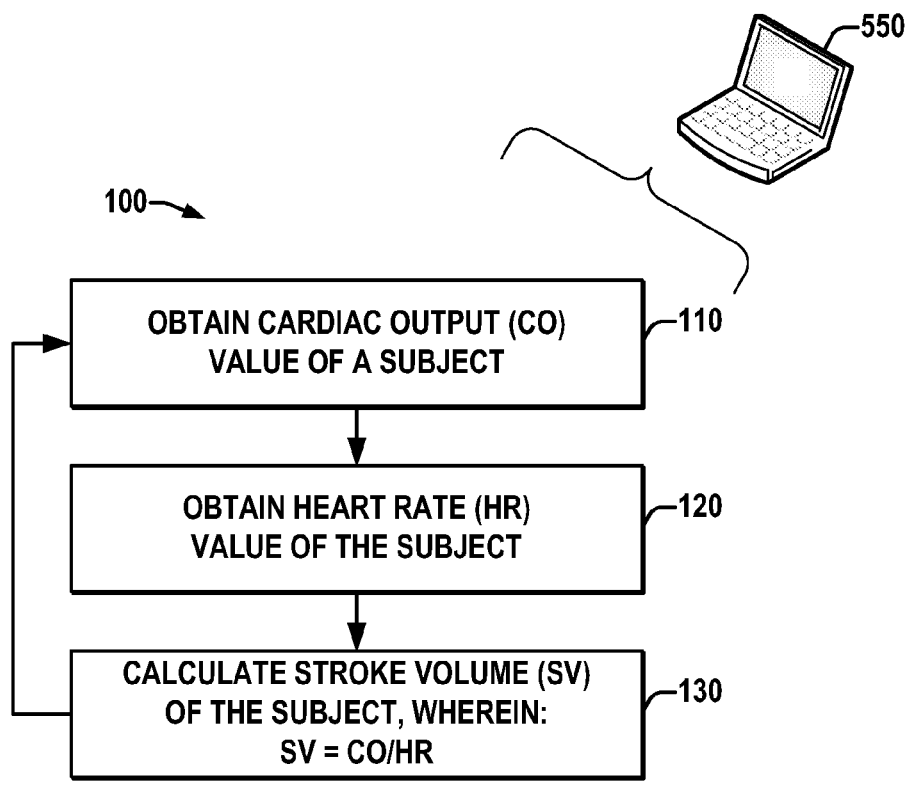
FIG. 1 illustrates a methodology to calculate the stroke volume of a subject.

The subject embodiments relate to systems and methods to utilize stroke volume (SV), mass, volume, velocity, and viscosity of blood and/or other cardiovascular data to influence the use of medication administered to a subject to treat hypertension and conditions related thereto. This cardiovascular data can be employed: to gauge the risk for potential adverse cardiovascular risk for an individual subject using a particular medication, within a clinical practice setting, and with other systems and methods to evaluate to use as a marker to alter treatment of a subject. In one example, the embodiments herein can be based upon an analysis of two or more antihypertensive medications, with equal BP lowering effects, but each with different effects upon SV and fluid retention, which is related thereto. Any candidate medications, however, are within the scope of the subject invention.

Some medical conditions and medications cause fluid retention. Fluid retention in turn can increase intravascular volume and pressure. When fluid retention occurs, some of the fluid is retained in the intravascular compartment. With normal vascular tone, and within limits, the cardiovascular system can vasodilate in order to accommodate the extra volume, and often there is no change in blood pressure (BP). BP can increase, however, if the cardiovascular system does not vasodilate enough to accommodate the extra volume and pressure, as occurs when vascular tone is compromised secondary to atherosclerotic disease as an example. As a result, cardiac output (CO) can increase following an increase in intravascular volume. When CO increases, SV, heart rate, or both, will increase.

Change in either BP or SV can influence the velocity of blood flow. The subject embodiments can be employed to calculate the effect of fluid retention upon velocity of blood flow, and then calculate how fluid retention influences whether blood is likely to flow in a turbulent or a laminar manner. The calculations discussed herein indicate that fluid retention has atherogenic consequences for the cardiovascular system regardless of whether or not the increased intravascular fluid increases BP.

SV, BP, mass of the blood, blood volume, velocity of blood flow, and viscosity of the blood, among other cardiovascular variables, can be used to quantify the effect of fluid retention upon turbulence of blood flow. In one approach, the Reynolds number is calculated using SV, density and viscosity of the blood to predict the likelihood that fluid will flow in a turbulent or a laminar manner. As fluid retention affects both the density and the viscosity of the blood, it can change the value of the Reynolds number. More particularly, the embodiments herein demonstrate that fluid retention increases both the mass and volume of the blood and decreases the viscosity of the blood—in addition to increasing stroke volume and/or BP. Because of its effects upon these variables, fluid retention increases the likelihood that blood will flow in a turbulent manner. To counter such adverse effects, diuretic medication can be employed to reduce or neutralize increased cardiovascular risk due to fluid retention.

Since changes in fluid retention may correlate with changes in SV, pharmaceutical agents that promote fluid retention are more likely to cause adverse cardiovascular events than pharmaceutical agents that do not cause fluid retention. The pharmaceutical classes of drugs that cause fluid retention include non-steroidal anti-inflammatory drugs (NSAIDs), cyclo-oxygenase-2 (COX-2) inhibitors, and thiazolidinedione (TZD) anti-diabetic medications. Medications in the COX-2 inhibitor and TZD pharmaceutical classes have been identified as increasing the risk of adverse cardiovascular events, and there is concern that non-selective NSAIDs increase the risk of cardiovascular disease. Conventional systems and methods do not consider changes in fluid retention nor changes in SV as mechanistically important in determining the cardiovascular effects of medications.

The reason that some medications, such as COX-2 inhibitors, nonselective non-steroidal anti-inflammatory drugs, estrogens, progestins, and rosiglitazone, are associated with an increased risk of myocardial infarctions and strokes can be related to fluid retention. Increased stroke volume and/or edema formation may indicate that a medication increases the risk of adverse cardiovascular events. For drugs that increase the risk of adverse cardiovascular events, it may be possible to reduce or neutralize the increased risk by simultaneously and/or subsequently administering a diuretic.

The subject examples discussed herein can lead to improvement in the cardiovascular safety of drug development and promotion of public health. Changes in SV and mass, volume and/or viscosity of blood or other cardiovascular markers may help identify the cardiovascular risk of pharmaceutical products at an early stage in the drug development process. A drug's effect upon particular cardiovascular markers could be determined prior to initiating expensive, prospective clinical trials. In one example, SV can be measured non-invasively via impedance cardiography along with other measurement techniques for different cardiovascular markers.

Increases in the degree of leg edema are due to fluid retention, and may thereby help identify the cardiovascular risk of pharmaceutical products at an early stage of the drug development process. Similarly, increases in natriuretic peptide levels, especially increases in B-natriuretic peptide levels, may help identify the cardiovascular risk of a pharmaceutical product at an early stage in the drug development process because natriuretic peptide levels are markers of intravascular volume. Likewise, abrupt increases in body weight following administration of a medication and/or abrupt increases in body mass following administration of a medication signify fluid retention, and may thereby help identify the cardiovascular risk of pharmaceutical products at an early stage of the drug development process.

If changes in certain cardiovascular markers influence atherosclerosis, a pharmaceutical manufacturer might choose to discontinue a drug based upon its effects upon SV, BP, mass of the blood, blood volume, viscosity of the blood, leg edema, body weight, and/or natriuretic peptide level, for example, thereby saving the expense of conducting a prospective trial. Furthermore, to the extent that clinical trials with drugs that could be predicted to cause cardiovascular complications are avoided, subject safety might improve. Finally, the embodiments described herein demonstrate that change in value of certain cardiovascular markers can be a risk factor for the development of atherosclerotic cardiovascular disease. Accordingly, it is reasonable to hypothesize that certain cardiovascular markers are previously unrecognized risk factors for the development of atherosclerosis as they all relate to fluid retention.

The embodiments described herein are not limited to cardiovascular markers that are indicative of fluid retention. For example, a candidate medication might increase cardiac contractility but have no effect upon fluid retention. Such a candidate medication would increase stroke volume when administered to patients or subjects, thereby signaling its potential to increase the risk of atherosclerotic cardiovascular disease.

In addition, the embodiments described herein are not limited to the utilization of any one cardiovascular marker by itself. The embodiments described herein apply to the simultaneous application of two or more cardiovascular markers. For example, the work done by the heart can be expressed as $W=P \cdot SV$, where W=work done by the heart, P=pressure at which the blood is ejected, and SV=stroke volume. Change in cardiac work may be a useful cardiovascular marker for gauging the risk of developing atherosclerotic cardiovascular disease. Accordingly, calculating a candidate medication's effect upon change in cardiac work may a useful metric for determining its cardiovascular risk within an individual's cardiovascular system.

As another example, cardiac output can be expressed as $CO=SV \cdot HR$, where CO=cardiac output, SV=stroke volume and HR=heart rate. Measuring or calculating cardiac output may be a useful cardiovascular marker for gauging the risk of developing atherosclerotic cardiovascular disease. Identifying a candidate medication's effect upon change in cardiac output may be a useful metric for determining its cardiovascular risk within an individual's cardiovascular system. Identifying a candidate medication's effect upon change in heart rate may be a useful metric for determining its cardiovascular risk within an individual's cardiovascular system.

FIG. 1 illustrates a methodology 100 to obtain a stroke volume from a subject. At reference numeral 110, a cardiac output value is obtained from the subject. The cardiac output can be obtained utilizing invasive and/or noninvasive methods. Invasive methods can include Fick technique, dye dilution, ultrasound dilution, pulmonary artery thermodilution, Doppler ultrasound, and pulse pressure methods. Noninvasive methods can include indirect Fick technique, impedance cardiography, electrical cardiometry, pulse pressure and magnetic resonance imaging.

The Fick technique involves calculating oxygen consumed over a given period of time from measurement of oxygen concentration of the venous blood and the arterial blood. Cardiac output (CO) can be calculated from: 1) volume of oxygen ($V_{O2}$) consumption per minute using a spirometer (wherein the subject is re-breathing air) and a $CO_2$ absorber, 2) oxygen or blood taken from the pulmonary artery (representing mixed venous blood and 3) the oxygen content of blood from a cannula in a peripheral artery (representing arterial blood). From these values the volume of oxygen can be calculated as:

$$VO2=(Q \times CA)-(Q \times CV) \quad \text{(Equation 1)}$$

where $C_A$ is the oxygen content of arterial blood and $C_V$ is the oxygen of venous blood.

Accordingly, CO is quantified as:

$$CO=(VO2/[CA-CV])*100 \quad \text{(Equation 2)}$$

The dye dilution method measures the concentration of a dye at different points in the circulatory system of a subject, usually from an intravenous injection and at a downstream sampling cite in a systemic artery. More particularly, the CO is equal to the quantity of marker die injected divided by the area under the dilution curve measured downstream (e.g. utilizing the Stewart-Hamilton equation) wherein:

$$\text{Cardiac output} = \frac{\text{Quantity of indicator}}{\int_0^\infty \text{Concentration of indicator} \cdot dt} \quad \text{(Equation 3)}$$

The ultrasound dilution method uses body temperature normal saline (NS) of a subject as a marker to measure cardiac output. Ultrasound Dilution technology is based on ultrasound marker dilution. Blood ultrasound velocity is a function of total blood protein concentration (e.g., sums of proteins in plasma and in red blood red cells), temperature etc. Injection of body temperature normal saline into a unique arteriovenous (AV) loop decreases blood ultrasound velocity to produce dilution curves. When the saline marker is injected into the AV loop, it is detected by the venous clamp-on sensor on the AV loop before it enters the subject's right heart atrium. After a marker transverses the heart and lung, the concentration curve in the arterial line is recoded and displayed. CO can then be calculated from the area of the concentration curve by the Stewart-Hamilton equation, which is well known in the art.

The pulmonary artery thermodilution method replaces the marker dye used in the dilution method with heated or cooled fluid wherein temperature change is measured at different sites in the circulation instead of dye concentration. A pulmonary artery catheter (PAC) is utilized to provide direct access to the right heart for thermodilution measurements. The PAC is ballooned tipped and is inflated, which allows the catheter balloon to "sail" through the right ventricle to occlude a smaller branch of the pulmonary artery system. At this point, the balloon is deflated. The PAC thermodilution method involves injecting a small amount (e.g., 10 ml) of cold glucose at a known temperature into the pulmonary artery and measuring the temperature of a known distance away (e.g., 6-10 cm) using the same catheter. The CO can be calculated from the measured temperature curve (thermodilution curve). A relatively high CO will change the temperature rapidly while a relatively low CO will change the temperature slowly.

The Doppler ultrasound method uses ultrasound and the Doppler effect to measure CO. The blood velocity through the heart causes a "Doppler shift" in the frequency of the returning ultrasound waves. This Doppler shift can then be used to calculate flow velocity and volume and effectively CO using the following equations:

$$CO=SV \times HR \quad \text{(Equation 4)}$$

$$SV=vti \times CSA \quad \text{(Equation 5)}$$

Where CSA is a valve orifice cross-sectional area, using $pr^2$; r is a valve radius; and vti is a velocity time integral of the trace of the Doppler flow profile.

The invasive pulse pressure method measures the pressure in an artery over time to derive a waveform and use this information to calculate cardiovascular performance. The method involves inserting a manometer (pressure sensor) into an artery, such as the radial or femoral artery, and continuously measuring the pulse pressure wave form. This can be done by connecting a catheter to a single processes and display device. The pulse pressure wave form can than be analyzed to provide measurements of cardiovascular performance, including CO.

An Indirect Fick Method measures CO by substituting $CO_2$ rather than $O_2$ into the Fick equation as follows:

$$CO=VCO_2(ml/min)/(CO_{2ART}-CO_{2VEN})(ml/L) \quad \text{(Equation 6)}$$

where $VCO_2$ (ml/min) is the rate of $CO_2$ production by the body and is determined using an Exercise Physiology System or Gas Analyzer and Spirometer. Modifications to this method include using inert gas as a tracer and measuring the change in inspired and expired gas concentrations to calculate CO.

Impedance cardiography is a method which calculates CO and SV from the measurements of changes in impedance across the chest over the cardiovascular cycle. Lower impedance indicates greater intrathoracic fluid volume and as the only fluid volume which changes beat to beat within the thorax is the blood, the change in impedance can be used to calculate the CO. In one example, total peripheral resistance can be measured utilizing only four paired electrodes, which are attached to the skin.

Electrical cardiometry is a non-invasive method similar to impedance cardiography. The difference is that electrical cardiometry attributes the steep increase of thoracic electrical bioimpedance beat-to-beat to the change in orientation of red blood cells. Four standard ECG electrodes are required for measurement of CO.

The non-invasive pulse pressure method measures the pressure in an artery over time to derive a waveform. This information is used to calculate CO. Arterial pressure (measured by sphygmomanometry) is reflective of the function of the heart and the CO associated therewith. The pressure in the heart rises as blood is forced into the aorta. The more the aorta is stretched, the greater the pulse pressure. In another embodiment, a more sophisticated pressure sensing device is employed against the skin surface to sense the pulsatile artery, wherein continuous PP waveforms are acquired non-invasively for analysis.

Finally, velocity encoded phase contrast Magnetic Resonance Imaging (MRI) is based on detection of changes in the phase of proton precession. These changes are proportional to the velocity of the movement of those protons through a magnetic field with a known gradient. The result of the MRI scan is two sets of images of each time point in the cardiovascular cycle. One is an anatomical image and the other is an image where the signal intensity in each pixel is directly proportional to the through-plane velocity. The average velocity in a vessel (e.g., the aorta or the pulmonary artery) is hence quantified by measuring the average signal intensity of the pixels in the cross section of the vessel and then multiplying by a known contrast. The flow is calculated by multiplying the mean velocity by the cross-sectional area of the vessel. This flow data can be used to graph flow versus time, which is used to calculate CO.

At 120, the heart rate value of the subject, defined as the number of heart beats per unit of time and typically expressed as beats per minute, is obtained. Heart rate can be measured by measuring the pulse of the subject at any point on the body where an artery pulsation is transmitted to the surface. In one example, an artery is compressed against an underlying structure (e.g., bone) by pressuring it with an index and middle finger.

The heart rate can be obtained from the subject in substantially any location on the body. Some examples that are commonly used are the radial artery, ulnar artery, carotid artery, brachial artery, femoral artery, posterior tibial artery, dosalis pedis, and popliteal artery. Alternatively or additionally, the pulse can be determined utilizing an electrocardiograph to provide continuous monitoring of a subject's heart.

At 130, the stroke volume (SV) of the subject is calculated using the CO obtained from step 110 and the heart rate (HR) obtained from step 120 using the following equation:

$$SV=CO/HR \quad \text{(Equation 7)}$$

The method returns to reference numeral 110 to obtain the CO and HR values of disparate subjects as necessary to calculate additional stroke volume values.

Figure 2:
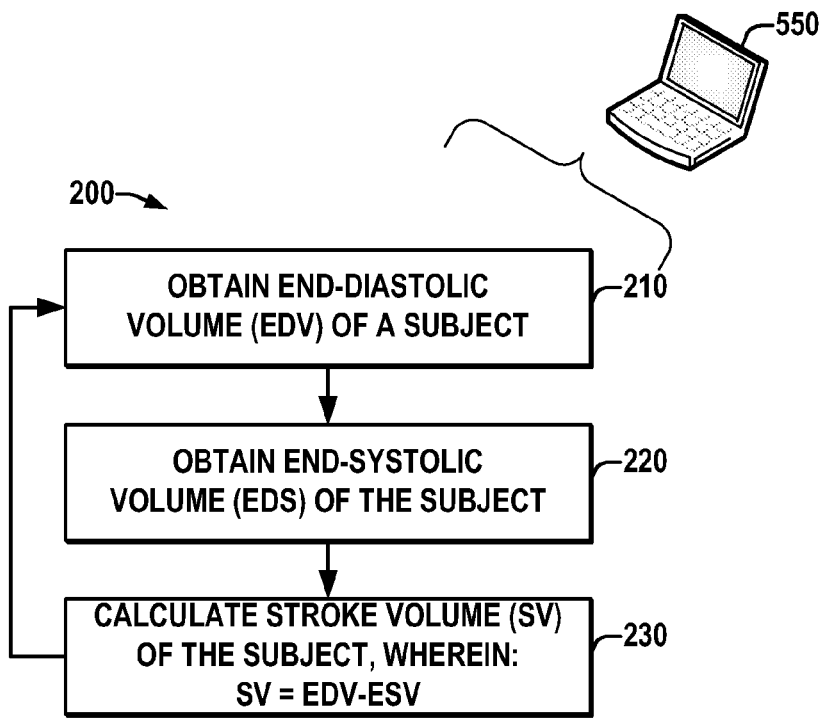
FIG. 2 illustrates an alternate methodology to calculate the stroke volume of a subject.

FIG. 2 illustrates a method 200 that can be utilized alternately or in addition to the method 100 above to obtain a stroke volume of a subject. At reference numeral 210, an end-diastolic volume (EDV) of a subject is obtained. The end-diastolic volume is the volume of blood in the ventricle at the end of a heartbeat and can be obtained utilizing known techniques. At 220, an end-systolic volume (ESV) of the subject is obtained. ESV is the volume of blood in the left ventricle at the end of contraction, or systole, and the beginning of filling, or diastole. ESV is the lowest volume of blood in the ventricle at any point in the cardiovascular cycle.

ESV can be used clinically as a measurement of the adequacy of cardiovascular emptying, related to systolic function. On an electrocardiogram, the ESV can be seen at the end of the T-wave. Clinically, ESV can be measured using two-dimensional echocardiography, MRI (magnetic resonance tomography), Multiple-Gated Acquisition (MUGA) Scan, or via a cardiovascular CT (computed tomography). Other known techniques to measure ESV are contemplated in association with embodiments described herein.

At 230, the EDV obtained at 210 and the ESV obtained at 220 is used to calculate stroke volume of a subject using the following formula:

$$SV=EDV-ESV \quad \text{(Equation 8)}$$

In one example, the subject has an EDV of 120 ml and an ESV of 50 ml. In this example, the stroke volume of the subject would be 120 ml−50 ml=70 ml. In one embodiment, the stroke volume data can be obtained from the subject both before administration of a medication and after an administration of a medication to determine any change thereof. Such change can be indicative of the potential effectiveness of the medication in mitigating hypertension and/or other cardiovascular abnormalities.

Figure 3:
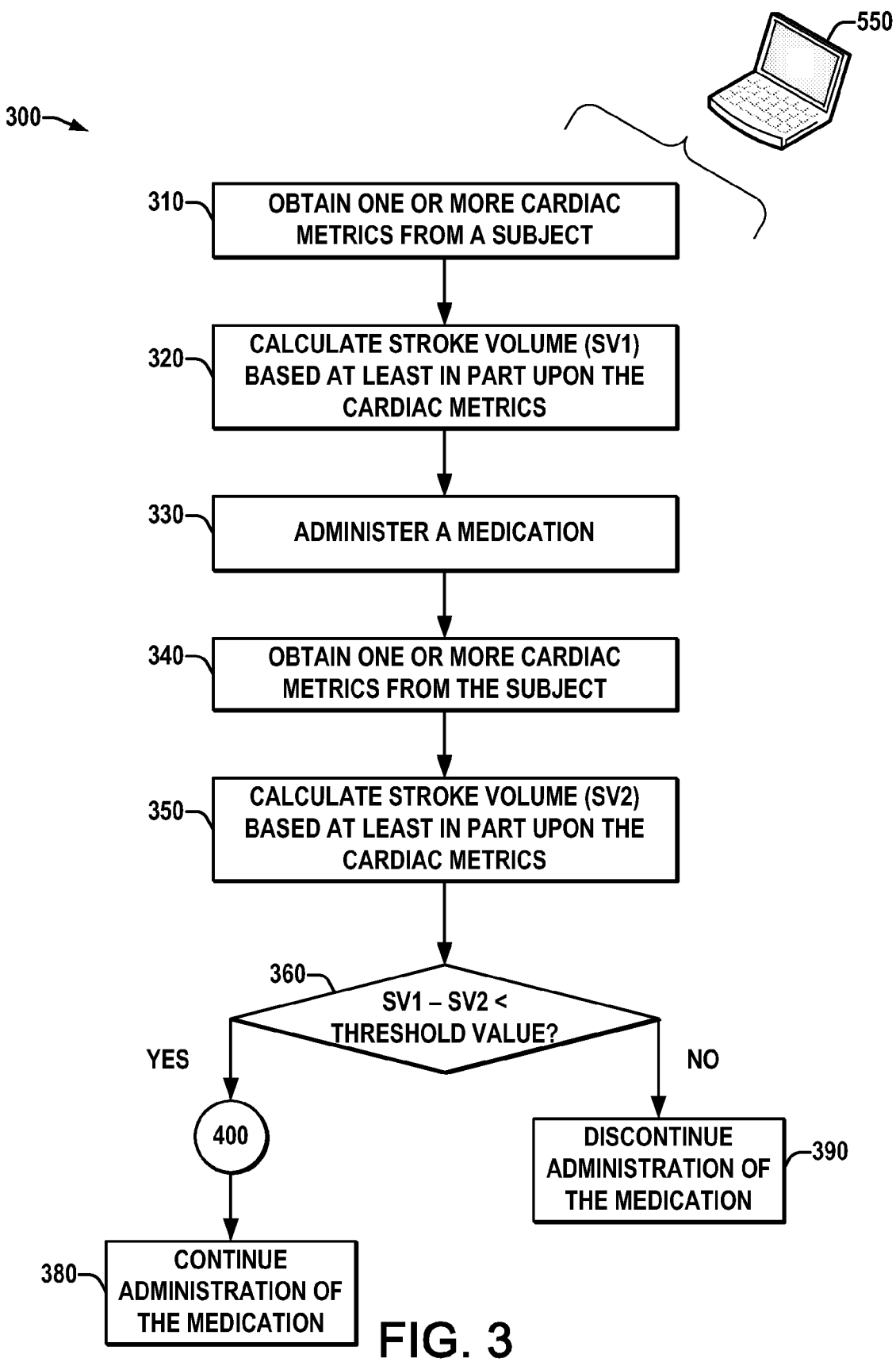
FIG. 3 illustrates a methodology to generally evaluate a candidate hypertensive medication's appropriateness for use as therapy for a given patient in clinical practice, based on that medication's effect on patient cardiac metrics and stroke volume.

FIG. 3 illustrates a methodology 300 that can be utilized within a clinical setting to evaluate the effectiveness of a medication on a subject. Once the effectiveness is established, a protocol can be evaluated and modified, if need be. At reference numeral 310, one or more cardiovascular markers are obtained from a subject. Such cardiovascular markers can include blood pressure, heart rate, cardiac output, stroke volume, blood volume, blood velocity, arterial wall elasticity, end-diastolic volume, and end-systolic volume. The markers can be obtained utilizing techniques discussed herein as appropriate for each marker.

At 320, a first stroke volume is calculated based at least in part upon the cardiovascular markers. In one embodiment, the stroke volume is calculated utilizing a cardiac output value and a heart rate value. In another embodiment, the stroke volume is obtained using an end-diastolic volume and an end-systolic volume. It is to be appreciated that substantially any known method, however, can be employed to calculate the stroke volume.

At 330 a medication is administered. The medication can relate to a formulation that is expected to modify cardiovascular behavior such as blood pressure. Alternatively, however, the formulation can be related to treatment of a condition unrelated to cardiovascular treatment wherein the cardiovascular system is nevertheless modified as a side effect of the medication. Various classes of medications may differ in their hemodynamic effects. For example, diuretics decrease SV, CCBs and β-blockers increase SV, and ACEIs have no effect upon SV. Accordingly, diuretics reduce cardiovascular disease more effectively than ACEIs, CCBs and β-blockers when the blood pressure lowering effect is comparable between the diuretic and the other classes of antihypertensive drugs. Basic principles of physics are applied to calculate the effect of changes in SV upon blood velocity and turbulence, to illustrate how SV influences atherosclerotic cardiovascular disease.

In either case, at 340, one or more cardiovascular markers are again obtained from the subject subsequent to medication administration. The cardiovascular markers obtained can be identical to the cardiovascular markers obtained in step 310. In this matter, calculations relating to particular markers, such as stroke volume can be normalized. At 350, a second stroke volume is calculated based on at least upon the cardiovascular markers obtained at step 340. Again, the stroke volume can be calculated utilizing known formulas including cardiac output, heart rate, end-diastolic volume and end-systolic volume.

At 360, a determination is made whether the difference between the first stroke volume and the second stoke volume is less than a predetermined threshold value. The threshold value can be set based upon expected results from the medication administered. In one example, the threshold value is particular to the subject under observation. Alternatively or in addition, the threshold value is based on a variation from a baseline, which is equal to the value of the first stroke volume. For instance, a variance of ten percent can be used as a threshold.

If the difference between the first stroke volume and the second stoke volume is less than the threshold value, administration of the medication is continued at step 380. If the difference between the first stroke volume and the second stroke volume is not less than the threshold value, however, administration of the medication is discontinued at 390. Continuing the above example, if the variation between the first and second stroke volumes is less than ten percent, administration of the medication is continued. If the variance between the first and second stroke volumes is greater than ten percent, administration of the medication is not continued.

Figure 4:
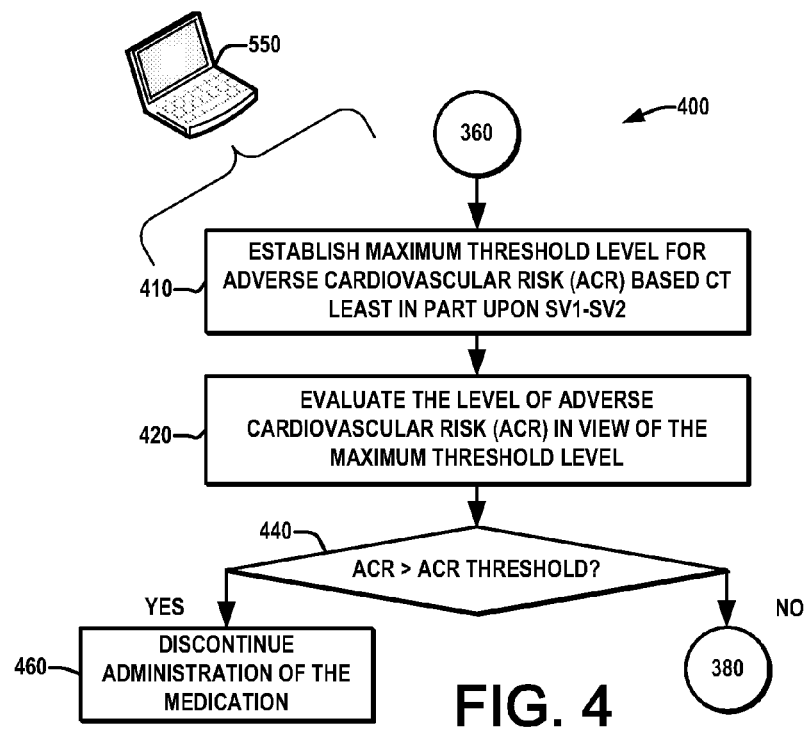
FIG. 4 illustrates a methodology to evaluate potential adverse cardiovascular risk for a subject based on stroke volume.

FIG. 4 illustrates a methodology 400 that can be utilized within the methodology 300 discussed above, wherein an input is received by the method 400 from step 360. At step 410, a maximum threshold level is established for adverse cardiovascular risk (ACR) based at least upon the difference between the first stroke volume and the second stroke volume. The ACR can be established based upon changes in one or more cardiovascular markers obtained from the subject in or based on the disparity between the stroke volume measured before and after administration of the medication (e.g., quantified as a percentage difference). ACR can also be set in view of one or more markers particular to the subject including age, gender, heredity, blood pressure level, elevated serum cholesterol level, lipoprotein level, tobacco use, weight, a biomarker such as a cardio-selective C-reactive protein level, and glucose intolerance.

At 420, the ACR level is evaluated in view of a maximum threshold level established at 410. At 440, if the ACR measured is greater than the ACR threshold, administration of the medication is discontinued at 360. If, however, the ACR is not greater than the ACR threshold, administration of the medication is continued at 380. By measuring the ACR for each subject during medication administration, deleterious effects of proposed medications can be mitigated.

Figure 5:
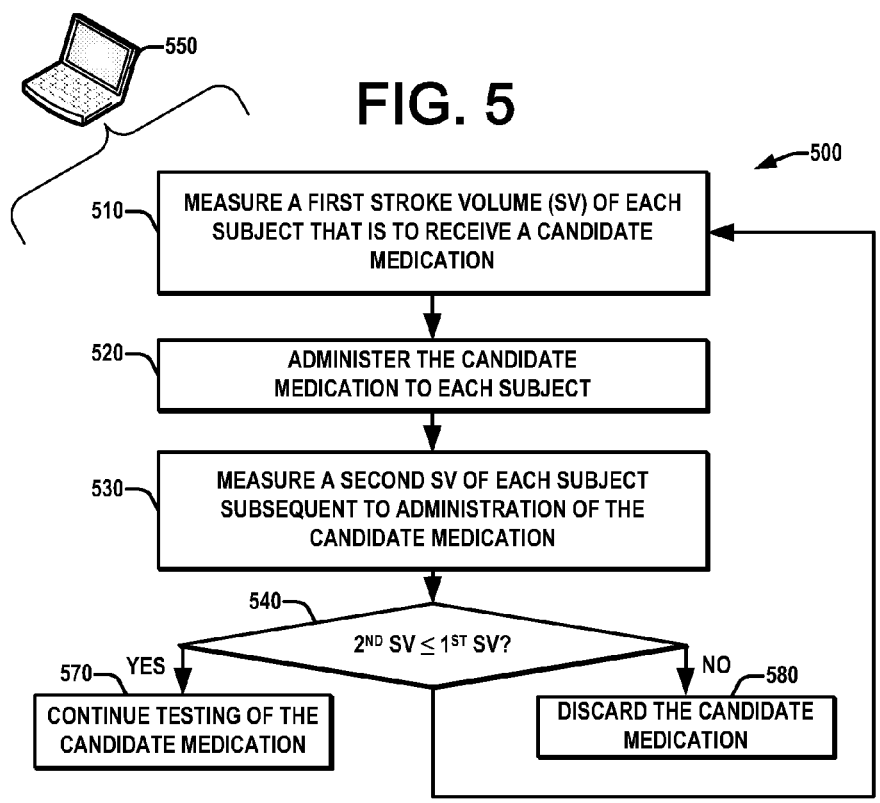
FIG. 5 illustrates a methodology to evaluate a candidate cardiovascular medication.

FIG. 5 illustrates a method 500 to determine if testing is to be continued for a candidate medication. At 510, a first stroke volume value is measured for each subject that is to receive a candidate medication. At 520, the medication is administered to each subject. At 530, a second stroke volume is measured for each subject subsequent to the administration of the candidate medication. If the second stroke volume is less than the first stroke volume, at 540, testing is continued 570 for the candidate medication. If the second stroke volume is not less than the first stroke volume, however, the candidate medication is discarded at 580. Regardless of the outcome, the method reverts back to reference numeral 510 to begin the examination of further disparate candidate medications.

The rationale for quantifying and comparing the stroke volume values before and after medication administration is related to the correlation between changes in SV, which alter the velocity of blood flow. Alterations in velocity of blood flow will influence turbulence. Changes in turbulence will affect endothelial function which, in turn, will influence the progression of atherosclerotic cardiovascular disease. Accordingly, SV may be a previously unrecognized risk factor for atherosclerotic cardiovascular disease.

If two medications lower BP equally but there are differences in stroke volume outcomes, then it is to be expected that differences in turbulence will manifest. This is physiologically relevant because atherosclerosis develops at arterial bifurcations and branch points, and it is at these locations that turbulence occurs. Turbulence promotes endothelial dysfunction. Therefore, if BP lowering effects are identical between two candidate medications, it is to be expected that differences in SV will influence atherosclerotic cardiovascular disease.

The line of reasoning has implications for medications that cause fluid retention. When fluid retention occurs, either cardiac output, BP, or both, will increase. An elevation in BP is detrimental to the cardiovascular system, but an increase in CO may also be detrimental, even if there is no change in BP. If CO increases, then either SV, heart rate, or both, will increase. To the extent that SV increases, turbulence at arterial bifurcations and branch points will increase, thereby accelerating endothelial dysfunction at these sites and promoting atherosclerotic cardiovascular disease. Examples of medications that cause fluid retention include non-steroidal anti-inflammatory drugs, COX-2 inhibitors, thiazolidinedione anti-diabetic medications, and insulin.

Blood is a heterogeneous fluid consisting mainly of plasma and a suspension of red blood cells. Red cells tend to aggregate when the flow shear rates are low, while increasing shear rates break these formations apart, thus reducing blood viscosity. This results in two non-Newtonian blood properties, shear thinning and yield stress. In healthy large arteries, blood can be successfully approximated as a homogeneous, Newtonian fluid since the vessel size is much greater than the size of particles and shear rates are sufficiently high that particle interactions may have a negligible effect on the flow. As such, blood flow in healthy vessels is generally laminar. In smaller vessels, however, non-Newtonian blood behavior should be taken into account. Thus, blood flow in diseased (e.g., atherosclerotic) arteries may be transitional or turbulent.

Mathematical Model

The work done by the heart can be expressed as $W = U_{BP} + KE + E_D$, where $W$=work, $U_{BP}$=the potential energy stored as blood pressure, KE=the kinetic energy of the blood, and $E_D$=the energy dissipated in the arterial walls by elastic recoil and relaxation. The energy dissipated in the arterial walls by elastic recoil is not likely to change appreciably for a given individual following a change in either $U_{BP}$ or KE. Thus, for any given individual, if a medication or disease state causes a change in the BP and/or the KE of the blood, the work done by the heart will change such that:

$$\Delta W = \Delta U_{BP} + \Delta KE \quad \text{(Equation 9)}$$

where $\Delta W$=change in work done by the heart, $\Delta U_{BP}$=change in potential energy stored as blood pressure, and $\Delta KE$=change in the kinetic energy of the blood.

The work done by the heart per stroke can be expressed as $W = P \cdot SV$, where P=pressure at which the blood is ejected, and SV=stroke volume. If the pressure at which the blood is ejected changes, and/or if SV changes, then the change in the work done by the heart per stroke can be represented as:

$$\Delta W = (\Delta P \cdot SV) + (P \cdot \Delta SV) + (\Delta P \cdot \Delta SV) \quad \text{(Equation 10)}$$

where $\Delta P$=change in pressure at which the blood is ejected, and $\Delta SV$=change in SV.

The kinetic energy of blood flow can be expressed as $$KE = \tfrac{1}{2} m \cdot v^2, \quad \text{(Equation 11)}$$

where m=mass of the blood, and v=velocity of blood flow. For any given individual, if there is a change in the kinetic energy of the blood, the change can be represented as:

$$\Delta KE = \tfrac{1}{2}[2(m \cdot v \cdot \Delta v) + m(\Delta v)^2 + \Delta m(v^2) + 2\Delta m \cdot v \cdot \Delta v + \Delta m \cdot (\Delta v)^2] \quad \text{(Equation 12)}$$

where $\Delta v$=change in the velocity of blood flow, and $\Delta m$=change in the mass of blood per stroke.

Combining Equation 12 with Equation 9 yields:

$$\Delta W = \Delta U_{BP} + \tfrac{1}{2}[2(m \cdot v \cdot \Delta v) + m(\Delta v)^2 + \Delta m \cdot v^2 + 2\Delta m \cdot v \cdot \Delta v + \Delta m \cdot (\Delta v)^2] \quad \text{(Equation 13)}$$

Combining Equation 13 with Equation 10 yields:

$$(\Delta P \cdot SV) + (P \cdot \Delta SV) + (\Delta P \cdot \Delta SV) = \Delta U_{BP} + \tfrac{1}{2}[2m \cdot v \cdot \Delta v + m(\Delta v)^2 + \Delta m \cdot v^2 + 2\Delta m \cdot v \cdot \Delta v + \Delta m \cdot (\Delta v)^2] \quad \text{(Equation 14)}$$

The calculus of variation of the kinetic energy in Equation 12 led to an expression in which appear terms of the second order that can be neglected. Thus, the change in kinetic energy in Equation 12 can be abbreviated to:

$$\Delta KE = \tfrac{1}{2}[2m \cdot v \cdot \Delta v + \Delta m \cdot v^2] \quad \text{(Equation 15)}$$

Similarly, some of the terms derived in Equation 10 are minute such that they can be ignored, and Equation 10 can be shortened to:

$$\Delta W = (\Delta P \cdot SV) + (P \cdot \Delta SV) \quad \text{(Equation 16)}$$

Therefore, Equation 14 can be simplified as follows:

$$(\Delta P \cdot SV) + (P \cdot \Delta SV) = \Delta U_{BP} + \tfrac{1}{2}[2m \cdot v \cdot \Delta v + \Delta m \cdot v^2] \quad \text{(Equation 17)}$$

Based upon Equation 17, if there is a change in the work done by the heart, there will be changes in BP, SV, velocity of blood flow, and the mass of blood per stroke that are interrelated.

Increased intravascular volume causes an increase in BP, an increase in SV, or an increase in both BP and SV. Based upon Equation 17, whenever BP alone increases, or SV alone increases, or BP and SV increase simultaneously, it is possible that the mass of blood per stroke will increase without any change in the velocity of blood flow. It is likely, however, that there will be some increase in the velocity of blood flow following an increase in intravascular volume.

This physical analysis is physiologically relevant because velocity of blood flow directly influences laminar flow. As the circulatory system is essentially a long cylinder, the Reynolds number (Re) can predict the likelihood that the fluid will flow in a laminar manner or a turbulent manner, as below:

$$Re = \frac{\rho d v}{\eta} \quad \text{(Equation 18)}$$

where $\rho$=fluid density, d=diameter of the cylinder, v=velocity of flow, and $\eta$=a viscosity factor that is unique to each fluid. An increase in intravascular volume decreases the density of the blood, increases the diameter of the blood vessels, increases the velocity of blood flow, and decreases the viscosity of the blood. It can be shown that an increase in intravascular volume will increase the Reynolds number of the blood.

If $Re_1$, $\rho_1$, $d_1$, $v_1$, and $\eta_1$=the initial Reynolds number, initial fluid density of the blood, initial diameter of the circulatory system, initial velocity of blood flow, and initial blood viscosity prior to an increase in intravascular volume, respectively, and $Re_2$, $\rho_2$, $d_2$, $v_2$, $\eta_2$=the Reynolds number, fluid density of the blood, diameter of the circulatory system, velocity of blood flow, and blood viscosity after an increase in intravascular volume, respectively, then the relationship between $Re_1$ and $Re_2$ can be expressed as:

$$\frac{Re_2}{Re_1} = \frac{\frac{\rho_2 d_2 v_2}{\eta_2}}{\frac{\rho_1 d_1 v_1}{\eta_1}} \quad \text{(Equation 19)}$$

Since $$\rho = \frac{\text{mass}}{\text{volume}},$$

radius (r) of a $$\text{cylinder} = \sqrt{\frac{\text{volume}}{\pi \cdot \text{length}}},$$

and d=2r, the relationship between $Re_1$ and $Re_2$ can also be expressed as:

$$Re_2 = Re_1 \cdot \frac{m_2}{m_1} \cdot \sqrt{\frac{vol_1}{vol_2}} \cdot \frac{\eta_1}{\eta_2} \cdot \frac{v_2}{v_1} \quad \text{(Equation 20)}$$

where $m_1$=the initial mass of blood, $m_2$=the mass of blood after an increase in intravascular volume, $vol_1$=the initial volume of blood, $vol_2$=the volume of blood after an increase in intravascular volume.

When intravascular volume increases, the ratio $$\frac{m_2}{m_1}$$

will be greater than 1, and the ratio $$\sqrt{\frac{vol_1}{vol_2}}$$

will be less than 1. For every milliliter that the plasma volume increases, the mass of the blood will increase 1.025 milligrams. Therefore, the product of $$\frac{m_2}{m_1} \cdot \sqrt{\frac{vol_1}{vol_2}}$$

will be greater than 1.

The viscosity of plasma is less than the viscosity of blood. When the intravascular volume increases, there will be an increase in plasma volume, and the viscosity of the blood in the intravascular compartment will decrease. As a result, the viscosity of the blood after an increase in intravascular volume will be less than the viscosity of the blood prior to the increase in intravascular volume, and $\eta_2$ will be less than $\eta_1$. Thus, following an increase in intravascular volume, the ratio $$\frac{\eta_1}{\eta_2}$$

will be greater than 1. Applying Equation 17, the ratio $$\frac{v_2}{v_1}$$

is likely to be greater than 1 following an increase in intravascular volume.

Using the ratios $$\frac{m_2}{m_1} \cdot \sqrt{\frac{vol_1}{vol_2}}, \frac{\eta_1}{\eta_2}, \text{ and } \frac{v_2}{v_1}$$

in Equation 20, when intravascular volume increases due to fluid retention, the new Reynolds number, $Re_2$, will be greater than the initial Reynolds number, $Re_1$. The higher the Re, the greater will be the propensity for a fluid to cross the threshold from laminar flow to turbulent flow. Consequently, fluid retention may increase the likelihood that blood will flow in a turbulent manner. Atherosclerosis develops at arterial bifurcations and branch points, and it is at these locations that turbulence occurs and turbulence promotes endothelial dysfunction. Accordingly, fluid retention can increase the development of atherosclerotic cardiovascular disease.

Data Associated with Exemplary Medications

There is experimental data to support the mathematical model developed discussed herein. Zhou et al studied the effect of aortic regurgitation upon atherosclerosis in mice. Mice with surgically-induced aortic regurgitation experienced no change in BP compared to their pre-surgical state, but the SV of mice with surgically-induced aortic regurgitation was greater than the SV of mice with normal aortic valves, and the mice with aortic regurgitation developed significantly more atherosclerotic lesions in their aortas than the mice with normal aortic valves.

Compared with other classes of antihypertensive agents, thiazide diuretics are the most effective first-line antihypertensive medications for preventing the occurrence of cardiovascular disease morbidity and mortality. While all antihypertensive medications lower BP, only diuretics decrease SV. Other classes of antihypertensive drugs either increase SV or have no effect upon SV.

The anti-diabetic medications, rosiglitazone and pioglitazone, promote fluid retention and increase SV. Since rosiglitazone is associated with an increased risk of adverse cardiovascular events while pioglitazone is associated with a decreased risk of adverse cardiovascular events, the discrepancy in adverse cardiovascular event outcomes between these two drugs appears to contradict the embodiments described herein. The explanation for this apparent contradiction may be that pioglitazone raises HDL-cholesterol, whereas rosiglitazone does not. HDL-cholesterol reduces atherosclerosis. If the mathematical calculations described herein accurately portray the effect of fluid retention upon atherosclerotic cardiovascular disease, it is conceivable that higher HDL-cholesterol levels due to pioglitazone compensate for the atherogenic effect of fluid retention.

Estrogen, both by itself or in combination with a progestin, promotes fluid retention and increases SV. Hormone replacement therapy with estrogen plus progestin is associated with an increased risk of cardiovascular death, non-fatal myocardial infarctions, and strokes. Second generation oral contraceptives, but not third generation oral contraceptives, are associated with an increased risk of myocardial infarcts and strokes.

While raloxifene increases SV, it has no effect upon the risk of coronary heart disease, cardiovascular death, or total stroke, but it may increase the risk of fatal stroke. Digoxin increases SV without altering BP. While digoxin neither increases nor decreases adverse cardiovascular events in subjects with heart failure, it may increase cardiovascular morbidity and mortality in some subsets of heart failure subjects.

A computer 550 illustrates one possible hardware configuration to support the systems and methods described herein, including the methods 100, 200, 300, 400, and 500 above. In order to provide additional context for various aspects of the present invention, the following discussion is intended to provide a brief, general description of a suitable computing environment in which the various aspects of the present invention may be implemented. Those skilled in the art will recognize that the invention also may be implemented in combination with other program modules and/or as a combination of hardware and software. Generally, program modules include routines, programs, components, data structures, etc., that perform particular tasks or implement particular abstract data types.

Moreover, those skilled in the art will appreciate that the inventive methods may be practiced with other computer system configurations, including single-processor or multi-processor computer systems, minicomputers, mainframe computers, as well as personal computers, hand-held computing devices, microprocessor-based or programmable consumer electronics, and the like, each of which may be operatively coupled to one or more associated devices. The illustrated aspects of the invention may also be practiced in distributed computing environments where certain tasks are performed by remote processing devices that are linked through a communications network. In a distributed computing environment, program modules may be located in both local and remote memory storage devices.

The computer 550 can utilize an exemplary environment for implementing various aspects of the invention including a computer, wherein the computer includes a processing unit, a system memory and a system bus. The system bus couples system components including, but not limited to the system memory to the processing unit. The processing unit may be any of various commercially available processors. Dual microprocessors and other multi-processor architectures also can be employed as the processing unit.

The system bus can be any of several types of bus structure including a memory bus or memory controller, a peripheral bus and a local bus using any of a variety of commercially available bus architectures. The system memory can include read only memory (ROM) and random access memory (RAM). A basic input/output system (BIOS), containing the basic routines that help to transfer information between elements within the computer 550, such as during start-up, is stored in the ROM.

The computer 550 can further include a hard disk drive, a magnetic disk drive, e.g., to read from or write to a removable disk, and an optical disk drive, e.g., for reading a CD-ROM disk or to read from or write to other optical media. The computer 550 can include at least some form of computer readable media. Computer readable media can be any available media that can be accessed by the computer. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other magnetic storage devices, or any other medium which can be used to store the desired information and which can be accessed by the computer 550.

Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer readable media.

A number of program modules may be stored in the drives and RAM, including an operating system, one or more application programs, other program modules, and program data. The operating system in the computer 550 can be any of a number of commercially available operating systems.

In addition, a user may enter commands and information into the computer through a keyboard and a pointing device, such as a mouse. Other input devices may include a microphone, an IR remote control, a track ball, a pen input device, a joystick, a game pad, a digitizing tablet, a satellite dish, a scanner, or the like. These and other input devices are often connected to the processing unit through a serial port interface that is coupled to the system bus, but may be connected by other interfaces, such as a parallel port, a game port, a universal serial bus ("USB"), an IR interface, and/or various wireless technologies. A monitor or other type of display device, may also be connected to the system bus via an interface, such as a video adapter. Visual output may also be accomplished through a remote display network protocol such as Remote Desktop Protocol, VNC, X-Window System, etc. In addition to visual output, a computer typically includes other peripheral output devices, such as speakers, printers, etc.

A display can be employed with the computer 550 to present data that is electronically received from the processing unit. For example, the display can be an LCD, plasma, CRT, etc. monitor that presents data electronically. Alternatively or in addition, the display can present received data in a hard copy format such as a printer, facsimile, plotter etc. The display can present data in any color and can receive data from the computer 550 via any wireless or hard wire protocol and/or standard.

The computer can operate in a networked environment using logical and/or physical connections to one or more remote computers, such as a remote computer(s). The remote computer(s) can be a workstation, a server computer, a router, a personal computer, microprocessor based entertainment appliance, a peer device or other common network node, and typically includes many or all of the elements described relative to the computer. The logical connections depicted include a local area network (LAN) and a wide area network (WAN). Such networking environments are commonplace in offices, enterprise-wide computer networks, intranets and the Internet.

When used in a LAN networking environment, the computer is connected to the local network through a network interface or adapter. When used in a WAN networking environment, the computer typically includes a modem, or is connected to a communications server on the LAN, or has other means for establishing communications over the WAN, such as the Internet. In a networked environment, program modules depicted relative to the computer, or portions thereof, may be stored in the remote memory storage device. It will be appreciated that network connections described herein are exemplary and other means of establishing a communications link between the computers may be used.

Figure 6:
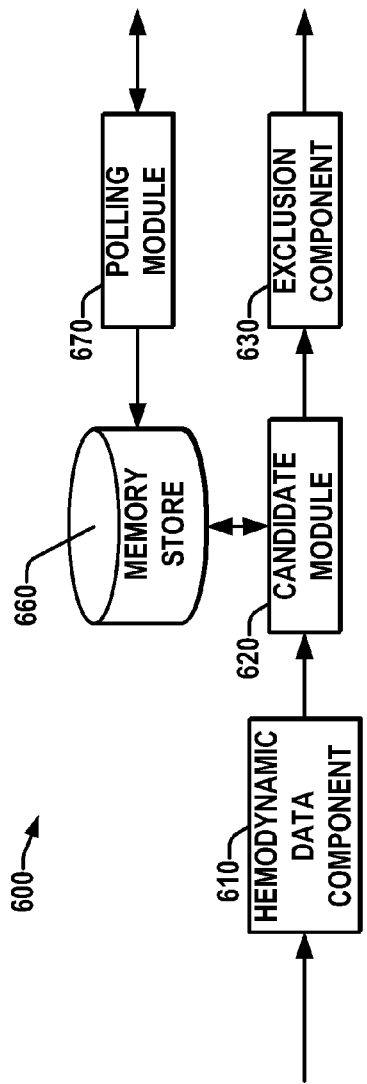
FIG. 6 illustrates a system to evaluate a candidate cardiovascular medication's appropriateness for use as therapy for a given patient in clinical practice, based on that medication's effect on patient cardiac metrics and stroke volume.

FIG. 6 illustrates a system 600 to evaluate a candidate cardiovascular medication. A hemodynamic data component 610 receives data from an outside source, which is utilized to determine whether to continue the research and development of one or more candidate medications. Substantially any data can be gathered that is related to cardiovascular markers of a test subject. Such data can include: cardiac output, intravascular volume, blood pressure, blood flow, mass of the blood, mass of the blood per stroke, density of the blood, volume of the blood, plasma volume, stroke volume, viscosity of the blood, serum osmolality, velocity of the blood, and/or turbulence of the blood. In one embodiment, data received by the hemodynamic data component 610 is gathered from a plurality of human test subjects, each of whom have been administered a particular candidate medication. In one example, the medication is formulated to potentially mitigate a hypertensive condition. The data can correspond to one or more cardiovascular markers that are observed both before and after the candidate medication is administered.

A candidate module 620 receives the data from the hemodynamic data component 610 and compares it to a predetermined threshold. If the value is less than the threshold, further evaluation of the medication can be recommended. If the value is greater than the predetermined threshold, a recommendation to discontinue evaluation can be output. An exclusion component 630 receives the recommendation from the candidate module 620 and can be employed to remove the candidate medication from further consideration (e.g., within a pool of candidates).

In one approach, the hemodynamic data component 610 receives information related to the disparity of a stroke volume (SV) for each subject. SV is the volume of blood pumped from one ventricle of the heart with each beat. It can be calculated by subtracting the volume of blood in the ventricle at the end of a beat (end-systolic volume) from the volume of blood just prior to the beat (end-diastolic volume). The disparity in SV can be determined before and after a candidate medication has been administered. The candidate module 620 can utilize a memory store 660 to retrieve a threshold that has been saved from a previous trial, study or sampling of subjects.

A polling module 670 can be utilized to perform real time polling of a plurality of subjects to identify a threshold for use by the memory store 660. The identification of a stroke volume differential that is below a predetermined threshold can be indicative of an ineffective formulation to prevent an atherosclerotic cardiovascular disease condition. A low differential may indicate a minimal decrease in stroke volume whereas a negative differential may indicate an increase in stroke volume after the candidate medication has been administered.

Figure 7:
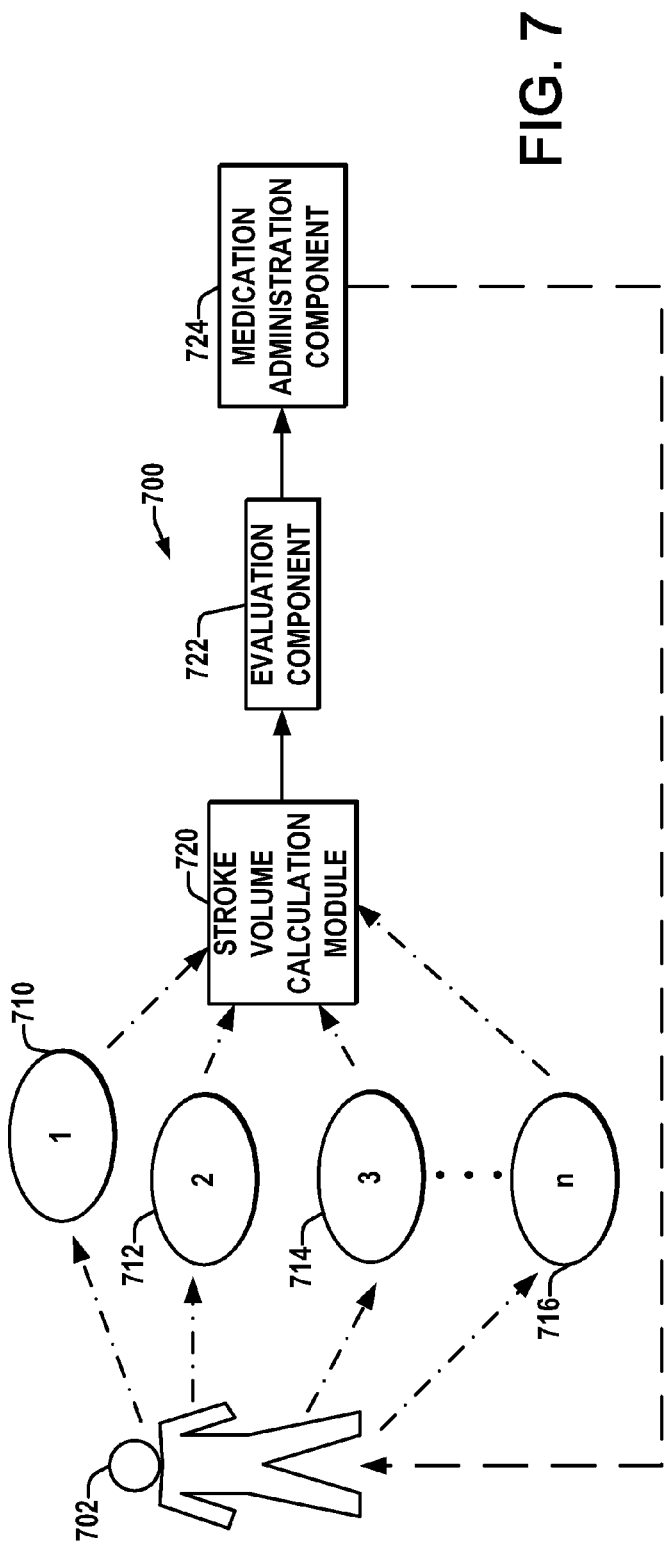
FIG. 7 illustrates a system used to evaluate and, if warranted, alter subject hypertension treatment based upon stroke volume of a subject.

FIG. 7 illustrates a system 700 used to evaluate and, if warranted, alter subject hypertension treatment based upon stroke volume of a subject 702. This determination can be based at least in part upon a change in stroke volume of the subject 702 both before and after a medication is administered. A plurality of cardiovascular markers are obtained from the subject 702 including: a first cardiovascular marker 710, a second cardiovascular marker 712, a third cardiovascular marker 714 and an nth cardiovascular marker 716. These markers can be related to substantially any cardiovascular markers such as blood pressure, stroke volume, blood volume, blood velocity and diastolic volume and end-systolic volume, heart rate and/or cardiac output.

The markers 710-716 are received by a stroke volume calculation module 720, which utilizes a program to execute a routine that calculates a stroke volume based on the markers 710-716. The calculation module 720 can contain a plurality of disparate calculation applications to adapt to a stroke volume calculation to the appropriate data type. For example, if end-diastolic volume and end-systolic volume markers are received, the calculation module 720 can utilize a first application to calculate the stroke volume. Alternatively, if a cardiac output and a heart rate are received, the calculation module can use a second application to calculate a stroke volume based on these data.

An evaluation component 722 receives the stroke volume calculated by the calculation module 720 for comparison to a predetermined threshold. If the evaluation component 722 determines that the stroke volume is at an acceptable level, it allows a medication administration component 724 to administer medication to the subject 702. If, however, the evaluation component 722 determines that the stroke volume received is not at an acceptable level, a control signal can be output to the medication administration component 724 to indicate that medication is not be administered to the subject 702.

The evaluation component 722 can determine an acceptable and an unacceptable level based upon data previously received from the subject 702. For example, an acceptable stroke volume level can be determined based upon a previous stroke volume obtained prior to administration of a medication. Alternatively or in addition, an acceptable level can be defined in terms of a variation (e.g., percentage difference) from a baseline value.

The medication administration component 724 receives the control signal from the evaluation component 722 and acts upon the control signal received. If the evaluation component sends a signal that indicates that medication is to be administered, the administration 724 facilitates delivery of the medication. If, however, the evaluation component indicates that medication is not to be administered, the administration component 724 does nothing. In one embodiment, the medication administration component 724 is an intravenous delivery system. In another embodiment, the administration component 724 is an automated pharmaceutical delivery system that identifies and locates particular requested medications and delivers them to a predetermined location.

Figure 8:
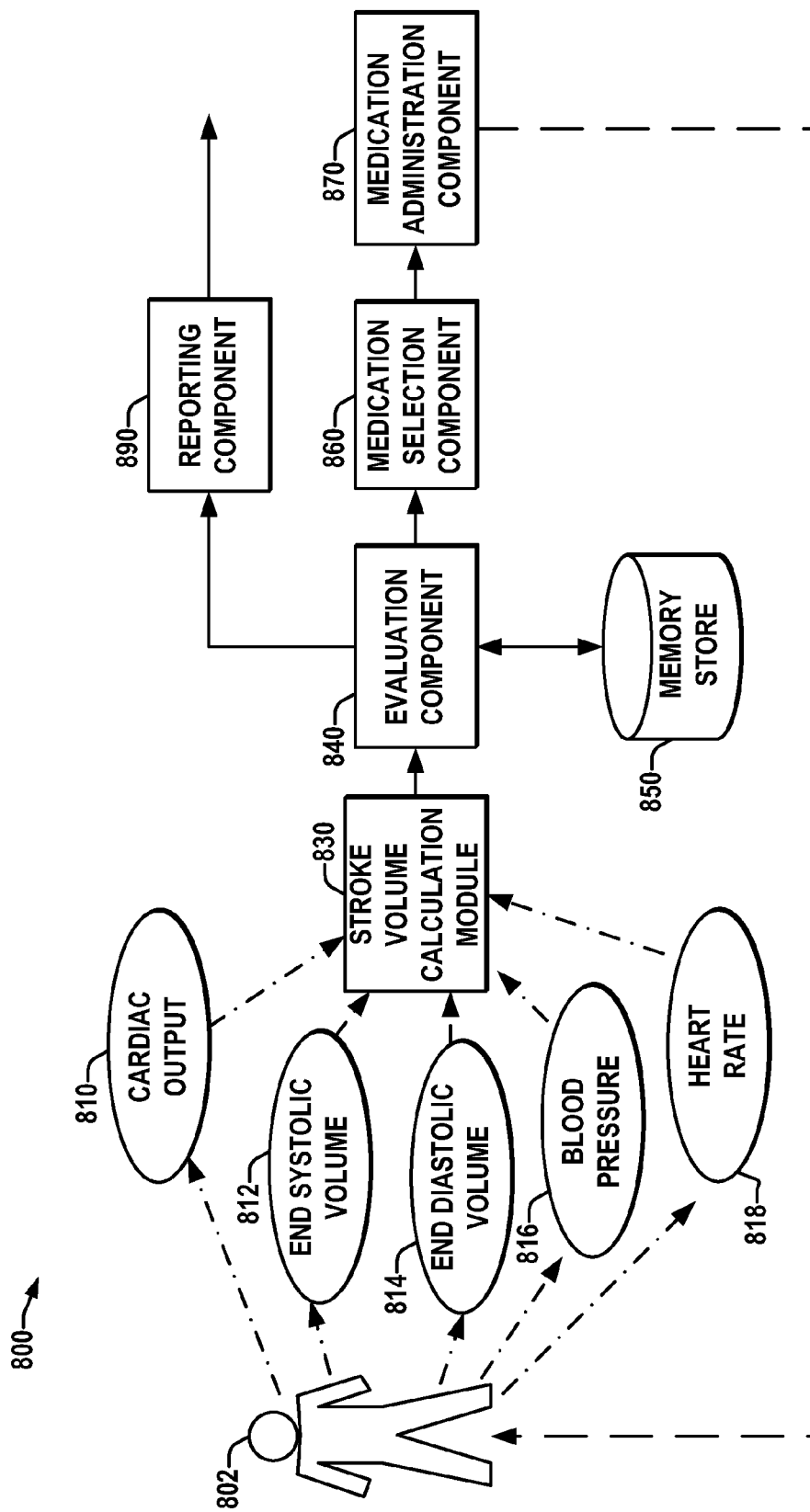
FIG. 8 illustrates a system to evaluate a subject based at least in part upon stroke volume during administration of cardiovascular medication.

FIG. 8 illustrates a system 800 to evaluate a subject 802 based at least in part upon the subject's stroke volume during administration of one or more cardiovascular medications. Once the evaluation is complete, a medication is selected to administer to the subject. In addition, a report can be generated that summarizes the evaluation of the cardiovascular condition of the subject 802 and recommended treatment thereof.

A cardiac output marker 810, an end-systolic volume marker 812 and an end-diastolic volume 814, a blood pressure marker 816 and a heart rate marker 818 are all obtained from the subject 802. These data are obtained as discussed herein utilizing appropriate technique for each data type. Once the markers 810-818 are obtained, a stroke volume calculation module 830 calculates a stroke volume of the subject 802 utilizing at least the one or more of the markers 810-818.

An evaluation component 840 receives the stroke volume calculated by the module 830 and determines the cardiovascular health of the subject 802 based at least in part upon a stroke volume provided by the module 830. To perform such an analysis, the evaluation component 840 is coupled to a memory store 850, which contains one or more of a look-up table, previous data related to the subject 802 previous data related to a current medication administered to the 802 and/or other relevant data that might be used to facilitate a cardiovascular health evaluation of the subject 802. Such previously collected data can provide a baseline from which to measure the newly collected data for comparison.

The evaluation component 840 can output information that is commensurate with one or more levels associated with the stroke volume calculation. In one example, a tier is associated with data that has a predetermined variance from a previous measurement. For instance, a first tier is associated with a 0-4% variance; a second tier is associated with a 5-9% variance; a third tier is associated with a 10-14% variance; a fourth tier is associated with a 15-20% variance, etc. In this manner, output from the evaluation component can include this tiered information to allow the medication selection component 860 to make a decision based on a more granular set of data for each subject.

A medication selection component 860 receives information from the evaluation component that relates to the subject 802. The medication selection component 860 can identify one or more medications that are recommended for use with the subject based at least in part upon the information received from the evaluation component 840. The selection performed can be related to a certain class of medication (e.g., hypertension, etc.) and/or related to particular condition experienced by the subject 802.

Once one or more medications have been selected by the selection component 860, a medication administration component 870 administers the one or more medications selected by the component 860. Once the medication has been administered, the markers 810-818 can again be obtained from the subject 802 to perform subsequent evaluations after administration of the medication.

A reporting component 890 receives a cardiovascular evaluation from the evaluation component 840 of the subject 802. The reporting component 890 can provide a summary and analysis for the cardiovascular health of the subject to utilize with the subject's medical record. In this manner, a tangible record of a subject cardiovascular health can be maintained to provide a "snap shot" of the subject's condition at a given point in time. The reporting component 890 can further contain editing tools to modify the appearance of a report output to modify the information contained therein.

Figure 9:
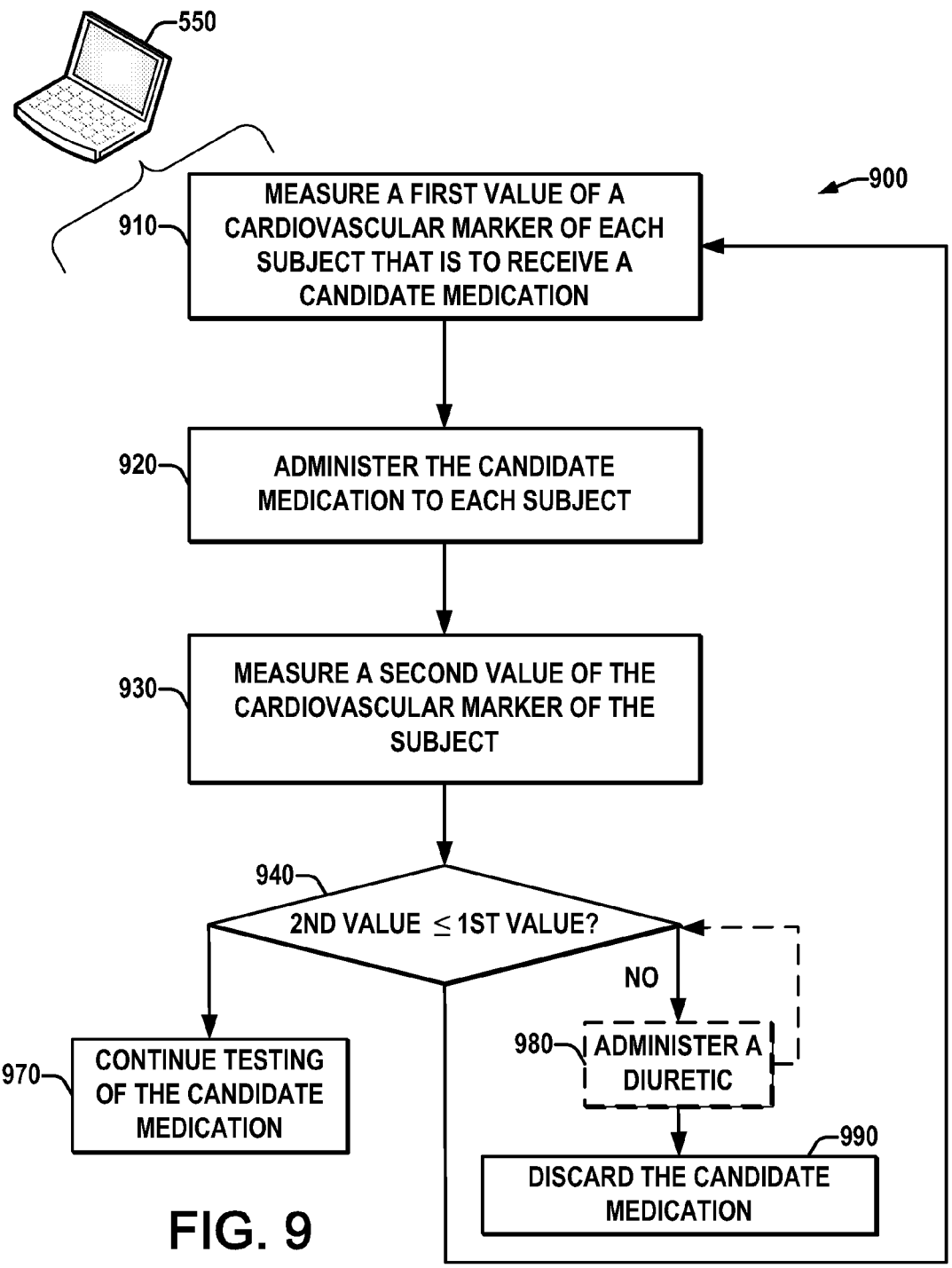
FIG. 9 illustrates a methodology to evaluate a candidate cardiovascular medication's appropriateness for use as therapy for a given patient in clinical practice, based on that medication's effect on patient cardiac metrics and stroke volume.

FIG. 9 illustrates a methodology to evaluate a candidate medication based on at least one cardiovascular marker. By measuring the at least one cardiovascular marker both before and after a medication is administered, the effect on such marker can be evaluated. At step 910, a first value of a cardiovascular marker is measured of each subject that is to receive a candidate medication. The cardiovascular marker can be one or more of a cardiac output, intravascular volume, blood pressure, blood flow, mass of the blood, mass of the blood per stroke, density of the blood, volume of the blood, plasma volume, SV, viscosity of the blood, serum osmolality, velocity of the blood, and/or turbulence of the blood for the subject.

At 920, the candidate medication is administered. The candidate medication administered can have an adverse affect on the one or more cardiovascular makers. For example, medications such as COX-2 inhibitors rofecoxib, valdecoxib, and parecoxib are associated with an increased risk of cardiovascular morbidity and mortality. In addition, nonselective nonsteroidal anti-inflammatory drugs (NSAIDs) can increase the risk of cardiovascular and cerebrovascular disease. The COX-2 inhibitors and nonselective NSAIDs cause fluid retention, which can increase the risk of atherosclerotic cardiovascular disease. Additionally, medications can cause edema, which is caused by fluid retention. Medications that cause edema include COX-2 inhibitors, nonselective NSAIDs, thiazolidinediones, sulfonylureas, insulin, glucocorticoids, estrogens, progestins, selective estrogen receptor modulators (tamoxifen, raloxifene), and anticonvulsants (gabapentin, pregabapentin, carbamazepine).

At 930, a second value of the cardiovascular marker of the subject is measured. If the first value is greater than or equal to the second value of the cardiovascular marker, at 940, testing of the candidate medication is continued at 970. If, however, the first value is less than the second value, one or more diuretic medications can optionally be administered at 980. Such diuretic can be used to lower fluid retention and thereby modify the value of one or more cardiovascular markers associated therewith. For example, administration of a diuretic can lower blood mass and/or volume of blood and/or BP and/or SV within a subject circulatory system as a result of the lower fluid retention. Other associated cardiovascular markers are contemplated within the scope of this invention.

The diuretic can be administered repeatedly if a desired result (e.g., second value is still greater than the first value) is not obtained. Alternatively or in addition, different types of diuretic medications can be administered to achieve a particular result. In one embodiment, the diuretic is administered along with the candidate medication at 920 regardless of whether it is administered at 980.

At 990, if the second value remains greater than the first value, the candidate medication is discarded and no further testing is conducted. In the event that measurement of a particular cardiovascular marker cannot be obtained directly, a suitable proxy marker can be used in place of a direct marker. For example, if measurement of velocity of blood flow is not obtainable, an SV measurement can be used in its place. The examples presented herein indicate that change in SV can increase development of atherosclerotic cardiovascular disease. Since there is a mathematical relationship between SV and velocity of blood flow, it is reasonable to hypothesize that SV itself is an unrecognized risk factor for the development of atherosclerotic cardiovascular disease. Similarly, a volume of blood within a subject circulatory system can be measured as a proxy for density of blood and/or viscosity of blood within the subject's circulatory system.

Figure 10:
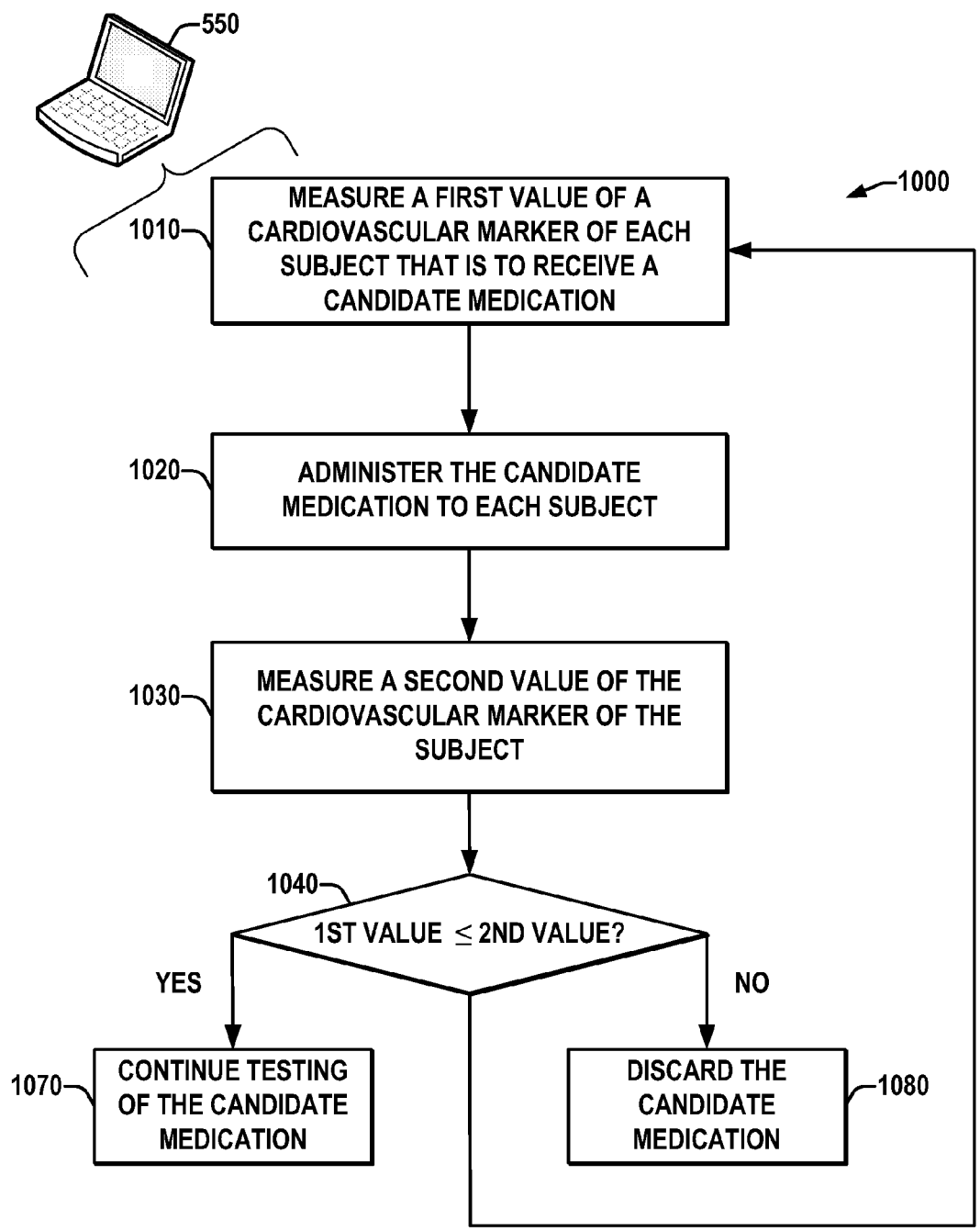
FIG. 10 illustrates a methodology to evaluate a candidate cardiovascular medication's appropriateness for use as therapy for a given patient in clinical practice, based on that medication's effect on patient cardiac metrics and stroke volume.

FIG. 10 illustrates a methodology 1000 that is utilized to continue testing of a candidate medication if a cardiovascular marker that increases subsequent to administering a candidate medication. At 1010, a first value of a cardiovascular marker of each subject is measured that is to receive a candidate medication. At 1020, the candidate medication is administered to each subject and, at 1030, a second value of the cardiovascular marker of the subject is measured. If the second value is greater than or equal to the first value, at 1040, testing of the candidate medication is continued at 1070. If, however, the second value is less than the first value, the candidate medication is discarded at 1080. One exemplary cardiovascular marker is viscosity of the subject's blood. If viscosity is decreased as a result of administration of the candidate medication, it can be indicative that fluid retention has also decreased. Accordingly, the candidate medication can be evaluated to provide favorable results by lowering the subject fluid retention within the circulatory system. In one embodiment, a diuretic or other medication can be utilized to lower fluid retention within a subject such that the diuretic and candidate medication are administered simultaneously to provide a favorable cardiovascular result.

Figure 11:
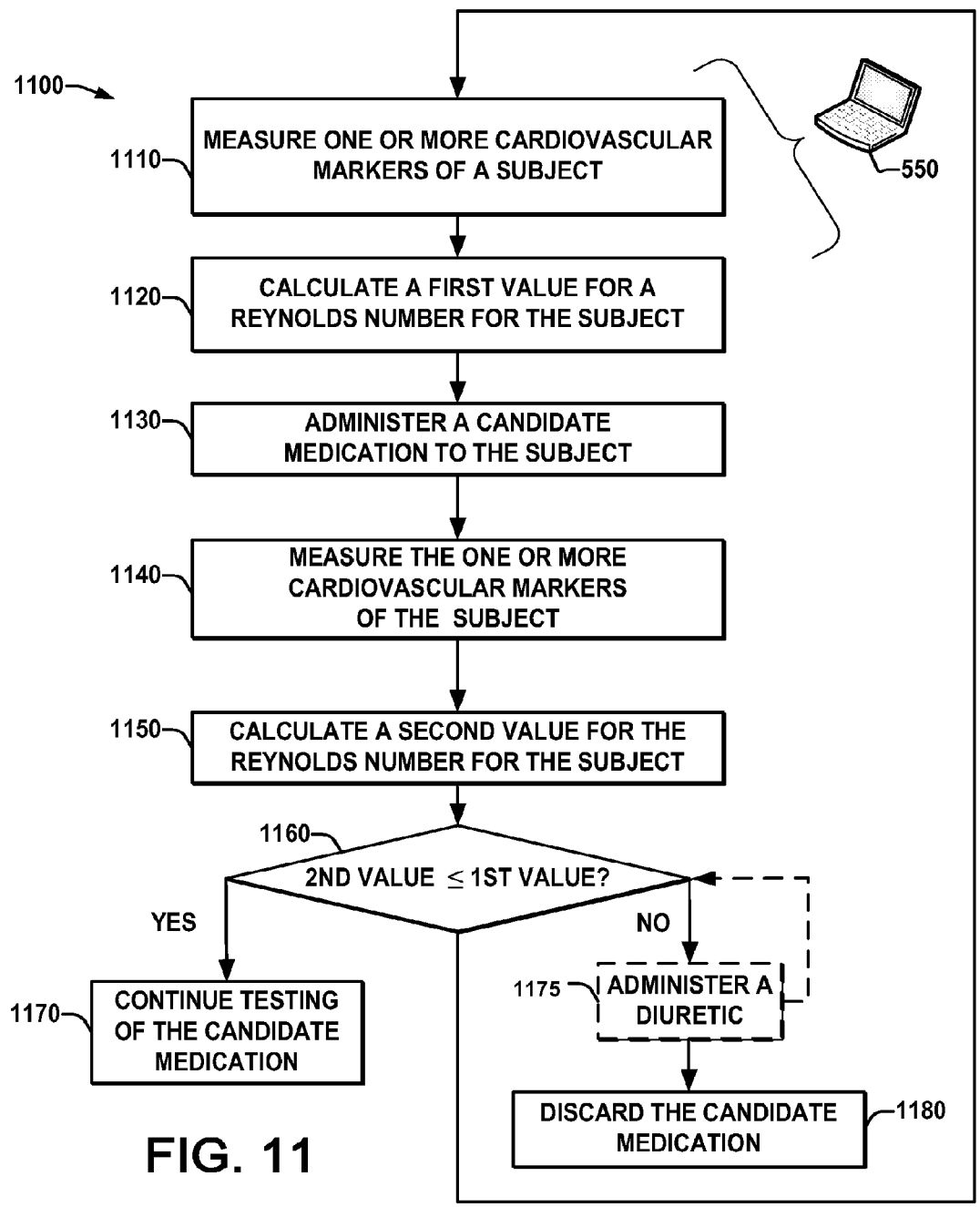
FIG. 11 illustrates a methodology to evaluate a candidate cardiovascular medication's appropriateness for use as therapy for a given patient in clinical practice, based on that medication's effect on patient cardiac metrics and stroke volume.

FIG. 11 illustrates a methodology 1100 to compare Reynolds numbers for a subject's circulatory to evaluate a candidate medication. At 1110, one or more cardiovascular markers are measured such as a fluid density of blood, a diameter of a circulatory system, a velocity of blood flow, and/or a blood viscosity. At 1120, a first value for a Reynolds number is calculated for the subject at least in part upon the measurements conducted at 1110. At step 1130, a candidate medication is administered to the subject. At 1140, a second set of measurements of the cardiovascular markers from step 1110 is taken. At 1150, a second value for a Reynolds number is calculated for the subject based upon the measurements taken at 1140.

If the first Reynolds number has a value that is greater or equal to the second Reynolds, at 1160, testing of the candidate medication is continued at 1170. This disparity it indicative of a reduction in fluid retention, which also lowers the likelihood of turbulent blood flow which can lead to atherosclerotic disease, as described herein. If, however, the first value is less than the second value, one or more diuretic medications can optionally be administered at 1170. Such diuretic can be used to lower fluid retention and thereby modify the value of one or more cardiovascular markers. The diuretic can be administered repeatedly if a desired result (e.g., second value is still greater than the first value) is not obtained. Alternatively or in addition, different types of diuretic medications can be administered to achieve a particular result. In one embodiment, the diuretic is administered along with the candidate medication at 1130 regardless of whether it is administered at 1170.

At 1180, if the second value of the Reynolds number remains greater than the first value, the candidate medication is discarded and testing is no longer continued at 1180. This can result because an increase in Reynolds number of a subject's circulatory system can be indicative of an increase in fluid retention, which is associated with turbulent blood flow. As such, there is a greater cardiovascular risk to administration of the medication.

The calculations discussed herein can be used to improve the safety of subjects in clinical trials, and also save pharmaceutical manufacturers time and money. Changes in SV and/or other cardiovascular markers can help identify the cardiovascular risk of pharmaceutical products at an early stage in the drug development process. A drug's effect upon SV can be determined prior to initiating expensive, prospective clinical trials. Pharmaceutical manufacturers might choose to discontinue a drug based upon its effects upon SV, thereby saving the expense of conducting prospective trials. To the extent that clinical trials with medications are employed to predict an increase in risk of cardiovascular disease, such medications can be avoided to improve the safety of subjects in clinical trials.

Figure 12:
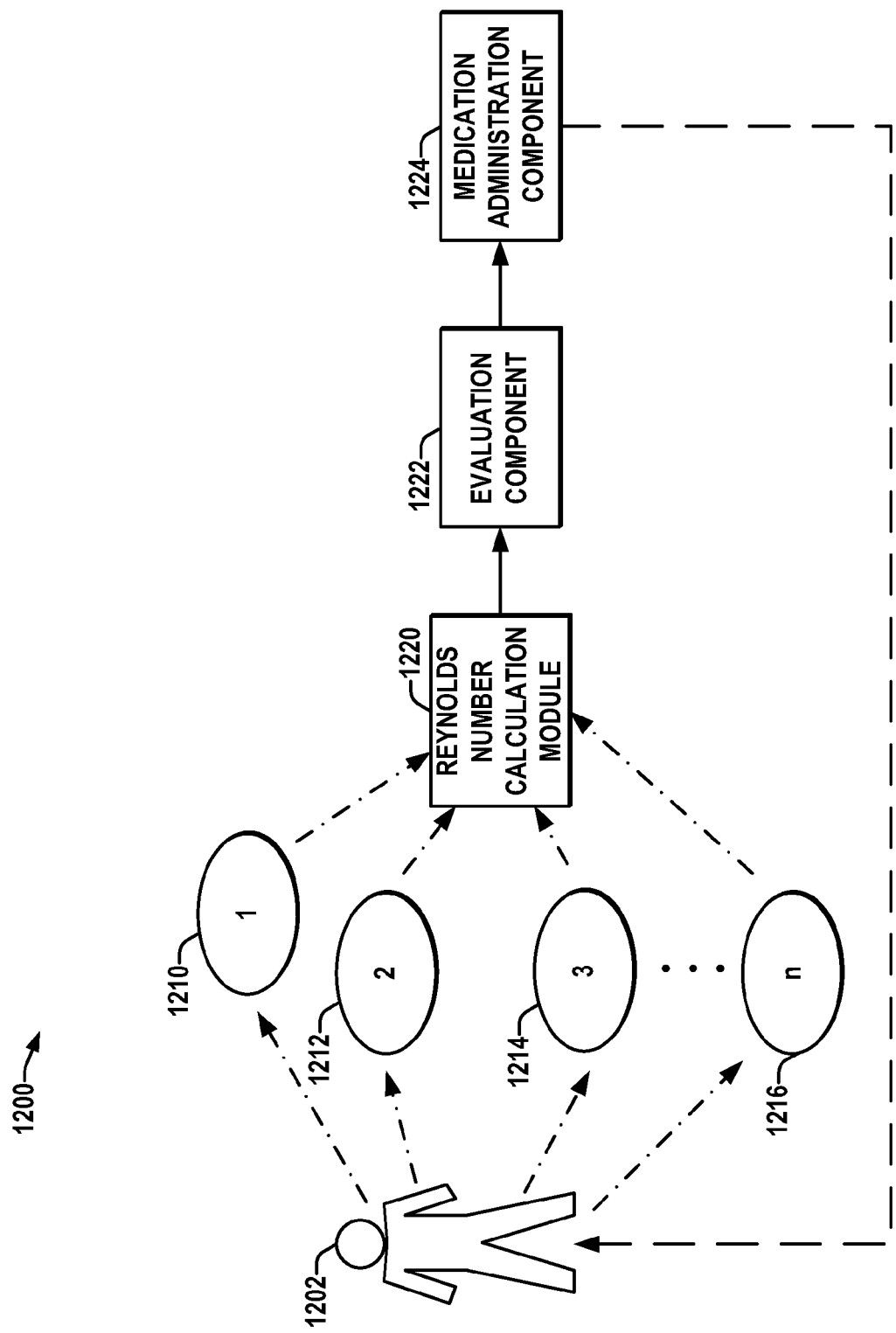
FIG. 12 illustrates a system used to evaluate and, if warranted, alter administration of a medication based upon Reynolds number of a subject circulatory system.

FIG. 12 illustrates a system 1200 used to evaluate and, if warranted, alter subject hypertension treatment based upon a Reynolds number associated with a subject 1202. This determination can be based at least in part upon a change in the Reynolds number of the subject 1202 both before and after a medication is administered. A plurality of cardiovascular markers is obtained from the subject 1202 including: a first cardiovascular marker 1210, a second cardiovascular marker 1212, a third cardiovascular marker 1214 and an nth cardiovascular marker 1216. These markers can be related to substantially any cardiovascular markers such as cardiac output, intravascular volume, blood pressure, blood flow, mass of the blood, mass of the blood per stroke, density of the blood, volume of the blood, plasma volume, stroke volume, viscosity of the blood, serum osmolality, velocity of the blood, and/or turbulence of the blood.

The markers 1210-1216 are received by a stroke volume calculation module 1220, which utilizes a program to execute a routine that calculates a Reynolds number based on the markers 1210-1216. The calculation module 1220 can contain a plurality of disparate calculation applications to facilitate calculation of a Reynolds number. For example, if a subject blood volume, blood mass, velocity of blood flow, blood viscosity, and circulatory system diameter are known, the Reynolds number can be calculated directly via $$Re = \frac{\frac{mass}{volume}dv}{\eta}$$

where d=diameter of the circulatory system, v=velocity of blood flow, and η=a viscosity factor of the blood. Alternatively, one or more proxy values can be used in place of direct variable values to calculate the Reynolds number. Such proxies can include SV as a proxy for velocity of blood flow and volume of blood within a subject circulatory system as a proxy for density and/or viscosity of blood within the subject circulatory system.

An evaluation component 1222 receives the stroke volume calculated by the calculation module 1220 for comparison to a predetermined threshold. If the evaluation component 1222 determines that the Reynolds number is at an acceptable level, it allows a medication administration component 1224 to administer medication to the subject 1202. If, however, the evaluation component 1222 determines that the Reynolds number received is not at an acceptable level, a control signal can be output to the medication administration component 1224 to indicate that medication is not be administered to the subject 1202.

The evaluation component 1222 can determine an acceptable and an unacceptable level based upon data previously received from the subject 1202. For example, an acceptable Reynolds number level can be determined based upon a previous Reynolds number calculated prior to administration of a medication. Alternatively or in addition, an acceptable Reynolds number value can be defined in terms of a variation (e.g., percentage difference) from a baseline.

The medication administration component 1224 receives the control signal from the evaluation component 1222 and acts upon the control signal received. If the evaluation component sends a signal that indicates that medication is to be administered, the administration 1224 facilitates delivery of the medication. If, however, the evaluation component indicates that medication is not to be administered, the administration component 1224 does nothing. In one embodiment, the medication administration component 1224 is an intravenous delivery system. In another embodiment, the administration component 1224 is an automated pharmaceutical delivery system that identifies and locates particular requested medications and delivers them to a predetermined location.

Using the systems and methods described herein, it may be possible to reduce the cardiovascular risk of drugs without cancelling production of every drug that increases SV, and without taking existing drugs off the market, even if it is recognized that a drug increases the risk of cardiovascular disease. If the property of a drug that increases its risk of cardiovascular disease is fluid retention, it may be possible to reduce or neutralize the increased cardiovascular risk by simultaneously administering a diuretic. This could be accomplished by packaging a diuretic along with the drug into a single pill, or else, once the drug is marketed, by simultaneously prescribing a diuretic along with the drug.

Given the availability of impedance cardiography, a technology that can non-invasively measure hemodynamic parameters, including SV. In practice, physicians could prescribe a drug that is known to increase the risk of cardiovascular disease, measure SV before and after administering the new drug, and then titrate the dose of a diuretic so as to lower the SV to baseline. Alternatively, when prescribing a drug that is recognized to increase the risk of cardiovascular disease, physicians might be able to reduce the cardiovascular risk by monitoring leg edema and body weight. Physicians could then titrate the dose of a diuretic so as to return the degree of leg edema and change in body weight to baseline. The choice of diuretic could be made based upon whether, in addition to reducing fluid retention, the desired effect included a reduction in BP or not.

By utilizing the embodiments herein described related to particular markers, the cardiovascular risk of pharmaceutical products can be identified at an early stage in a drug development process. Further, the effectiveness of particular medications can be evaluated clinically with individual subjects, wherein treatment is modified based on such evaluation. In addition, SV can be considered an independent risk factor for atherosclerotic cardiovascular disease. Thus, the embodiments described herein can contribute to subject safety, and it may benefit pharmaceutical manufacturers as well as certain government administrative entities.

In summary, embodiments described herein are employed to measure cardiovascular markers associated with fluid retention. Change in the value of these markers can be indicative of increased fluid retention within a subject cardiovascular system, which can increase the likelihood that blood will flow in a turbulent manner. Increased turbulence, in turn, will promote endothelial dysfunction, thereby contributing to the development of atherosclerotic cardiovascular disease.

The examples have been described with reference to the preferred embodiments. Obviously, modificatterions and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. A system to evaluate safety of a medication, comprising:
an evaluation component adapted to measure a first cardiovascular marker associated with a circulatory system of a subject and a second cardiovascular marker associated with the circulatory system of the subject to determine a fluid retention value based at least in part upon the cardiovascular markers received, wherein the first cardiovascular marker is measured before the medication is administered to the subject and wherein the second cardiovascular marker is measured after the medication is administered, and wherein the first and second cardiovascular markers include at least one cardiovascular marker selected from the group consisting of stroke volume of the circulatory system of the subject, mass of blood per heart stroke of the subject, a volume of blood within the circulatory system of the subject, a plasma volume within the circulatory system of the subject, a turbulence of blood flow within the circulatory system of the subject, a velocity of blood flow within the circulatory system of the subject, a fluid retention measurement associated with the circulatory system of the subject, an intravascular volume of the circulatory system of the subject, a degree of leg edema of the subject, a body weight of the subject, a body mass of the subject, a nutriuretic peptide level of the subject, a blood pressure of the subject, a pressure at which the blood is ejected from the heart of the subject, a cardiac work of the subject, a cardiac output of the subject, viscosity of blood within the circulatory system of the subject, serum osmolality within the circulatory system of the subject, density of blood within the circulatory system of the subject, Reynolds number associated with the circulatory system of the subject;

a memory store adapted to store the first and second cardiovascular markers from the subject, the memory store also receives subject information selected from the group consisting of age, gender, heredity, blood pressure, serum cholesterol level, lipoprotein level, tobacco use, subject weight, a biomarker, and glucose intolerance;

wherein the evaluation component is in communication with the memory store and a reporting component, the evaluation component determines a fluid retention threshold based on at least the subject information, the evaluation component also evaluates the cardiovascular health of the subject by comparing the fluid retention value to the fluid retention threshold, and wherein if the fluid retention value is greater than the fluid retention threshold, the evaluation component provides an evaluation to the reporting component containing a recommendation to discontinue use of the medication;

wherein the first cardiovascular marker and second cardiovascular marker includes a calculation of a Reynolds number, wherein the evaluation component calculates the Reynolds number using at least one of cardiac output, intravascular volume, blood pressure, blood flow, mass of the blood, mass of the blood per stroke, density of the blood, volume of the blood, plasma volume, stroke volume, viscosity of the blood, serum osmolality, velocity of the blood, and turbulence of the blood of the subject.

2. A system to evaluate safety of a medication, comprising:

an evaluation component adapted to measure a first cardiovascular marker associated with a circulatory system of a subject and a second cardiovascular marker associated with the circulatory system of the subject to determine a fluid retention value based at least in part upon the cardiovascular markers received, wherein the first cardiovascular marker is measured before the medication is administered to the subject and wherein the second cardiovascular marker is measured after the medication is administered, and wherein the first and second cardiovascular markers include at least one cardiovascular marker selected from the group consisting of stroke volume of the circulatory system of the subject, mass of blood per heart stroke of the subject, a volume of blood within the circulatory system of the subject, a plasma volume within the circulatory system of the subject, a turbulence of blood flow within the circulatory system of the subject, a velocity of blood flow within the circulatory system of the subject, a fluid retention measurement associated with the circulatory system of the subject, an intravascular volume of the circulate system of the subject, a degree of leg edema of the subject, a body weight of the subject, a body mass of the subject, a nutriuretic peptide level of the subject, a blood pressure of the subject, a pressure at which the blood is ejected from the heart of the subject, a cardiac work of the subject, a cardiac output of the subject, viscosity of blood within the circulatory system of the subject, serum osmolality within the circulatory system of the subject, density of blood within the circulatory system of the subject, Reynolds number associated with the circulatory system of the subject;

a memory store adapted to store the first and second cardiovascular markers from the subject, the memory store also receives subject information selected from the group consisting of age, gender, heredity, blood pressure, serum cholesterol level, lipoprotein level, tobacco use, subject weight, a biomarker, and glucose intolerance;

wherein the evaluation component is in communication with the memory store and a reporting component, the evaluation component determines a fluid retention threshold based on at least the subject information, the evaluation component also evaluates the cardiovascular health of the subject by comparing the fluid retention value to the fluid retention threshold, and wherein if the fluid retention value is greater than the fluid retention threshold, the evaluation component provides an evaluation to the reporting component containing a recommendation to discontinue use of the medication;

wherein the evaluation component determines the difference between the fluid retention threshold and fluid retention value as a fluid retention percentage, and wherein the system further includes a medication selection component in communication with the evaluation component to receive the fluid retention percentage from the evaluation component, the medication selection component includes a first tier of 0-4%, a second tier of 5-9%, a third tier of 10-14% and a fourth tier of 15-20%, the medication selection component being adapted to recommend an alternative medication from a plurality of alternative medications based on the tier in which the fluid retention percentage falls and communicate the alternative medication recommendation to the reporting component.

3. The system of claim 2, wherein the first and second cardiovascular marker is a stroke volume.

* * * * *